United States Patent
Seibold et al.

(10) Patent No.: US 8,147,513 B2
(45) Date of Patent: *Apr. 3, 2012

(54) APPARATUS FOR SEALING SURGICAL PUNCTURES

(75) Inventors: Gerd Seibold, Ammerbuch (DE); Kenneth J. Michlitsch, Livermore, CA (US); Randolf Von Oepen, Los Altos Hills, CA (US); Bodo Quint, Rottenberg (DE); Ib Erling Joergensen, Haigerloch (DE); Stevan Nielsen, Rottenberg (DE); Tommy Conzelmann, Rangendingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 323 days.

This patent is subject to a terminal disclaimer.

(21) Appl. No.: 12/117,556

(22) Filed: May 8, 2008

(65) Prior Publication Data

US 2008/0208225 A1    Aug. 28, 2008

Related U.S. Application Data

(63) Continuation of application No. 10/523,166, filed as application No. PCT/EP03/08248 on Jul. 25, 2003.

(60) Provisional application No. 60/400,658, filed on Jul. 31, 2002.

(51) Int. Cl.
*A61B 17/08* (2006.01)
(52) U.S. Cl. .................................................. 606/215
(58) Field of Classification Search .............. 606/200, 606/215–217, 213, 214, 218
See application file for complete search history.

(56) References Cited

U.S. PATENT DOCUMENTS

| | | | |
|---|---|---|---|
| 5,061,274 A | 10/1991 | Kensey | |
| 5,108,420 A | 4/1992 | Marks | |
| 5,334,217 A | 8/1994 | Das | |
| 5,425,744 A | 6/1995 | Fagan et al. | |
| 5,531,759 A * | 7/1996 | Kensey et al. | 606/213 |
| 5,725,552 A | 3/1998 | Kotula et al. | |
| 5,797,960 A * | 8/1998 | Stevens et al. | 606/213 |
| 5,879,366 A | 3/1999 | Shaw et al. | |
| 5,944,738 A | 8/1999 | Amplatz et al. | |
| 6,080,182 A | 6/2000 | Shaw et al. | |
| 6,214,029 B1 | 4/2001 | Thill et al. | |
| 6,258,091 B1 * | 7/2001 | Sevrain et al. | 606/301 |
| 6,537,300 B2 | 3/2003 | Girton | |

(Continued)

FOREIGN PATENT DOCUMENTS

EP    1147743    10/2001

(Continued)

OTHER PUBLICATIONS

U.S. Appl. No. 12/117,581, filed May 8, 2008, Seibold et al.

(Continued)

*Primary Examiner* — Gary Jackson
*Assistant Examiner* — Eric Blatt
(74) *Attorney, Agent, or Firm* — Workman Nydegger

(57) ABSTRACT

Apparatus is provided for sealing a puncture within a vessel or tissue to provide hemostasis, comprising a first disk coupled to either a second disk or a spring, and sealingly engaged to the vessel or tissue surrounding the puncture. At least the first disk is preferably configured to substantially conform to the profile of the vessel or tissue when deployed. In one embodiment, the disks may be released from engagement with the vessel or tissue to reposition the disks after deployment.

24 Claims, 11 Drawing Sheets

U.S. PATENT DOCUMENTS

| | | |
|---|---|---|
| 6,551,344 B2 | 4/2003 | Thill |
| 6,596,013 B2 | 7/2003 | Yang et al. |
| 6,911,037 B2 | 6/2005 | Gainor et al. |
| 6,949,113 B2 | 9/2005 | Van Tassel et al. |
| 7,223,280 B2 | 5/2007 | Anson et al. |
| 7,431,729 B2 | 10/2008 | Chanduszko |
| 2003/0009180 A1 | 1/2003 | Hinchliffe et al. |
| 2003/0055455 A1 | 3/2003 | Yang et al. |
| 2003/0191497 A1 | 10/2003 | Cope |
| 2005/0277983 A1 | 12/2005 | Saadat et al. |
| 2006/0106418 A1 | 5/2006 | Seibold et al. |

FOREIGN PATENT DOCUMENTS

| | | |
|---|---|---|
| WO | WO9313712 | 7/1993 |
| WO | WO9802100 | 1/1998 |
| WO | WO9847430 | 10/1998 |
| WO | WO0117435 | 3/2001 |
| WO | WO2004012603 | 2/2004 |

OTHER PUBLICATIONS

U.S. Appl. No. 10/523,166, filed Oct. 10, 2007, Office Action.
U.S. Appl. No. 10/523,166, filed Apr. 1, 2008, Office Action.
U.S. Appl. No. 10/523,166, filed Nov. 19, 2008, Office Action.
U.S. Appl. No. 60/400,658, filed Jul. 31, 2002, Michlitsch et al.
U.S. Appl. No. 10/523,166, filed Jul. 21, 2009, Office Action.
U.S. Appl. No. 10/523,166, filed Apr. 27, 2010, Office Action.
U.S. Appl. No. 12/117,581, filed Aug. 3, 2010, Office Action.
U.S. Appl. No. 10/523,166, filed Mar. 3, 2011, Office Action.
U.S. Appl. No. 12/117,581, filed Mar. 3, 2011, Office Action.
U.S. Appl. No. 10/523,166, mailed Oct. 12, 2011, Notice of Allowance.
U.S. Appl. No. 12/117,581, mailed Oct. 7, 2011, Notice of Allowance.

* cited by examiner

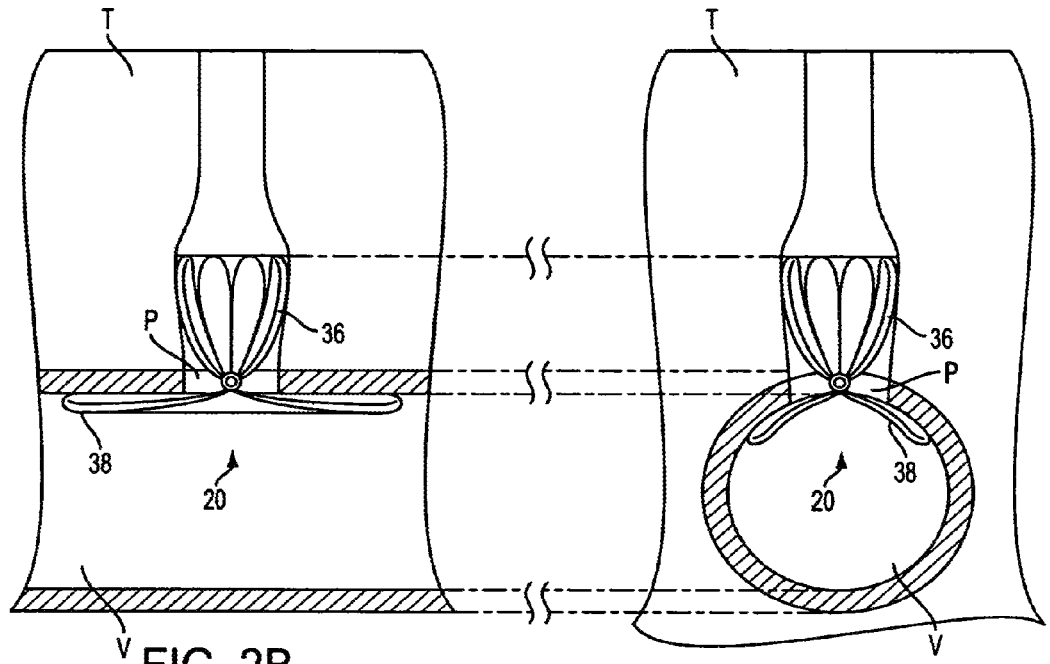
FIG. 2B
FIG. 2C
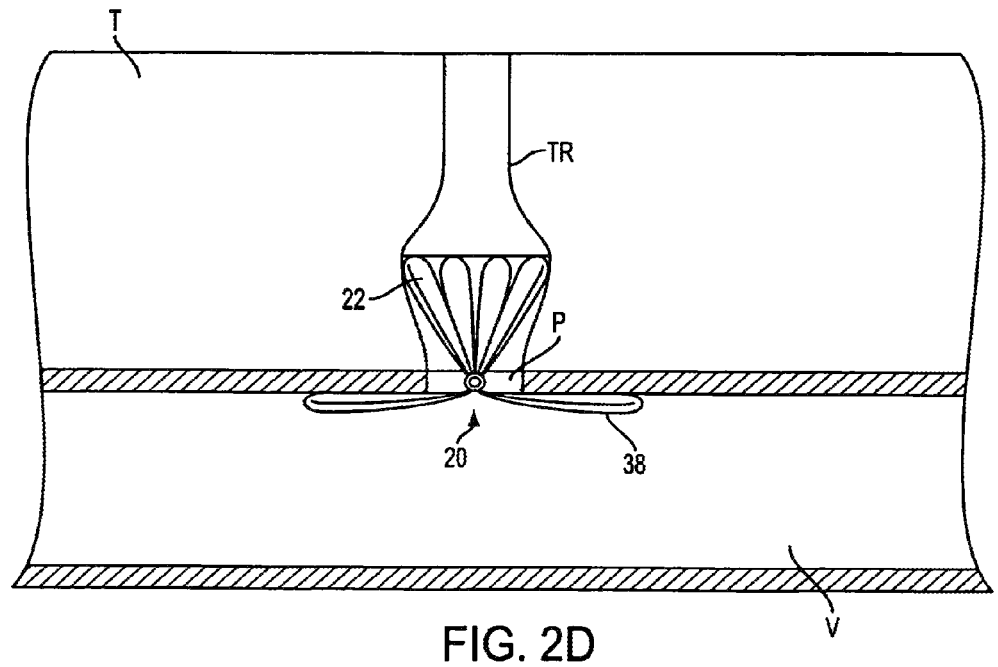
FIG. 2D

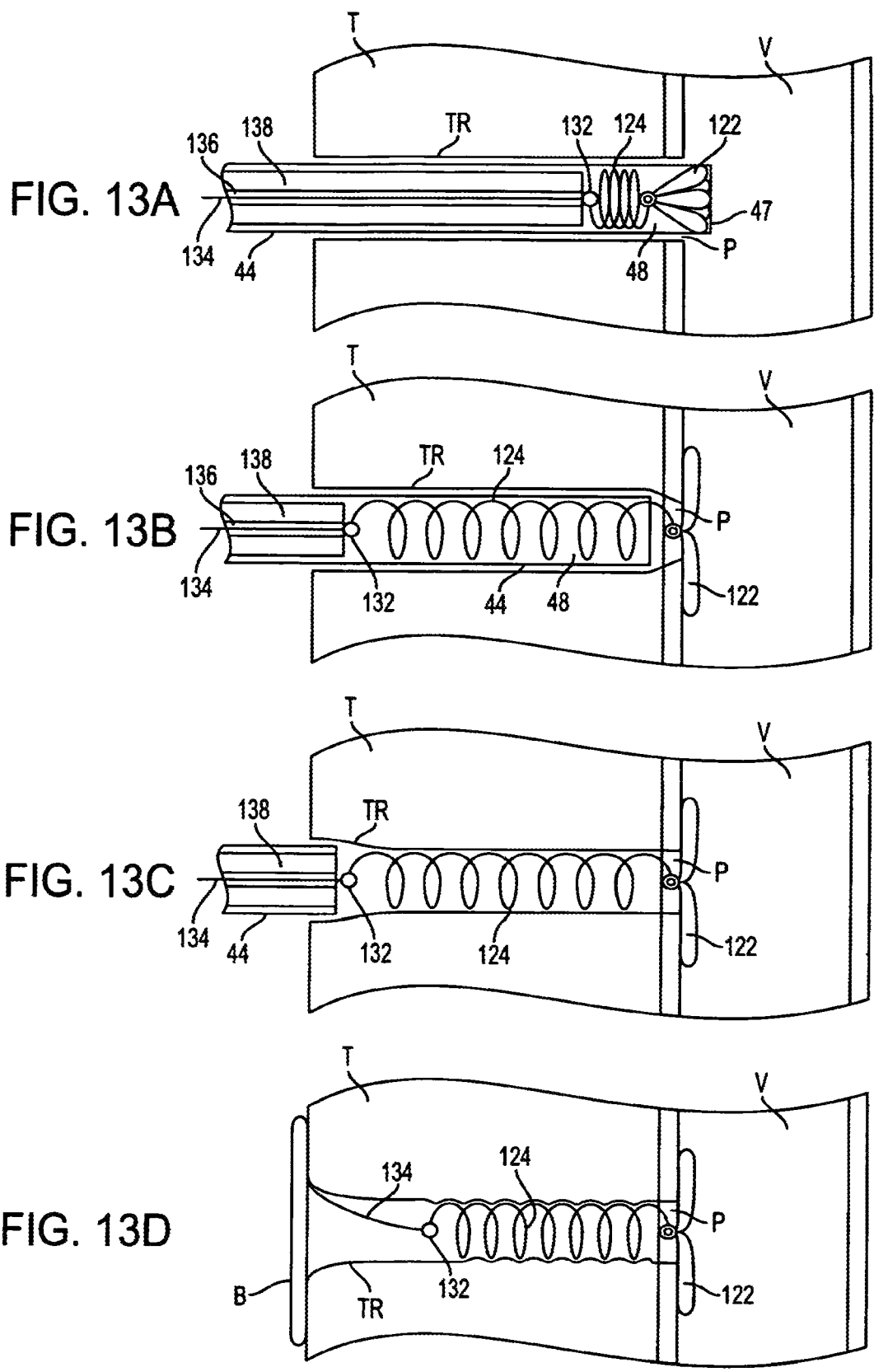

APPARATUS FOR SEALING SURGICAL PUNCTURES

CROSS-REFERENCE TO RELATED APPLICATIONS

This application is a continuation of U.S. patent application Ser. No. 10/523,166, filed Dec. 2, 2005, which is a §371 Nationalization of Patent Cooperation Treaty Application Serial No. PCT/EP03/08248, filed Jul. 25, 2003, which claims the benefit of U.S. Provisional Patent Application Ser. No. 60/400,658 filed Jul. 31, 2002, the disclosures of which are each incorporated by reference herein.

FIELD OF THE INVENTION

The present invention relates to apparatus for sealing punctures in vessels and tissue. More specifically, the invention relates to a self-expanding device that is inserted to sealingly engage a vessel or tissue surrounding a puncture.

BACKGROUND OF THE INVENTION

A large number of medical diagnostic and therapeutic procedures involve the percutaneous introduction of instrumentation into the blood vessel. For example, coronary angioplasty, angiography, atherectomy, stenting, and numerous other procedures often involve accessing the vasculature through placement of a catheter or other device in a patient's femoral artery or other blood vessel. Once the procedure is completed and the catheter or other diagnostic or therapeutic device is removed, bleeding from the resultant vascular puncture must be stopped.

Traditionally, a medical practitioner applies external pressure to the puncture site to stem bleeding until hemostasis occurs (i.e. when the clotting and tissue rebuilding have sealed the puncture). This method, however, presents numerous problems. In some instances, this pressure must be applied for up to an hour or more, during which time the patient is uncomfortably immobilized. In addition, there exists a risk of hematoma since bleeding from the puncture may continue until sufficient clotting occurs, particularly if the patient moves during the clotting process. Furthermore, application of external pressure to stop bleeding may be unsuitable for patients with substantial amounts of subcutaneous adipose tissue since the skin surface may be a considerable distance from the puncture site, thereby rendering external compression less effective.

Another traditional approach to subcutaneous puncture closure comprises having a medical practitioner internally suture the vessel puncture. This method, however, often requires a complex procedure and requires considerable skill by the medical practitioner.

Apparatus and methods also are known in which a plug is introduced into the vessel puncture, to cover the puncture and promote hemostasis. Various types of plugs have been proposed. One example is described in U.S. Pat. No. 5,061,274 to Kensey, comprising a plug made from animal-derived collagen. Such apparatus may be unsuitable for some patients due to an adverse immunological reaction to animal-derived collagen. Furthermore, a plug inserted into the puncture may be dislodged into the vessel during the healing process due to the application of pressure to the wound, potentially causing stenosis of the vessel.

Mechanical occlusion devices have been proposed for sealing, e.g., atrial septal defects, and typically comprise two expandable disks that sealingly compress tissue surrounding the hole. One such device is described in U.S. Pat. No. 5,425,744 to Fagan et al. That device has several drawbacks: (1) it does not permit the device to be repositioned once it is deployed at the puncture without inflicting additional trauma on the engaged tissue; and (2) when deployed into a vessel, the device may protrude into the blood stream, thereby disturbing blood flow and causing thrombosis of the vessel.

In view of these drawbacks, it would be desirable to provide apparatus for sealing a puncture within a vessel or tissue that provides a low profile when engaged against the vessel or tissue wall.

It also would be desirable to provide apparatus for sealing a puncture within a vessel or tissue that is biodegradable.

It further would be desirable to provide apparatus for sealing a puncture within a vessel or tissue that decreases the likelihood of dislodgement of the apparatus.

It still further would be desirable to provide apparatus for sealing a puncture within a vessel or tissue that would permit a medical practitioner to reposition the apparatus after it has been deployed, without inflicting additional trauma to the vessel or tissue.

SUMMARY OF THE INVENTION

In view of the foregoing, it is an object of the present invention to provide apparatus for sealing a puncture within a vessel or tissue that provides a low profile when engaged against the vessel or tissue wall.

It also is an object of the present invention to provide apparatus for sealing a puncture within a vessel or tissue that is biodegradable.

It further is an object of the present invention to provide apparatus for sealing a puncture within a vessel or tissue that decreases the likelihood of dislodgement of the apparatus.

It even further is an object of the present invention to provide apparatus for sealing a puncture within a vessel or tissue that would permit a medical practitioner to reposition the apparatus after it has been deployed, without inflicting additional trauma to the vessel or tissue.

These and other objects of the present invention are accomplished by providing apparatus for sealing a puncture within a vessel or tissue that comprises at least partially self-expanding occlusion elements that may be inserted through the puncture to sealingly engage the vessel or tissue surrounding the puncture.

In a first embodiment, the occlusion element comprises a pair of connected disks having self-expanding wire frames optionally encased by a flexible, fluid impermeable membrane. Each wire frame comprises a plurality of petals, and expands from a contracted delivery configuration to a deployed configuration, in which the disks sealingly engage the vessel or tissue surrounding the puncture.

In a second embodiment, the occlusion element comprises a nut and a bolt, wherein each of the nut and bolt has a disk that includes a self-expanding wire frame optionally encased by a flexible, fluid impermeable membrane. Each wire frame comprises a plurality of petals that expand from a contracted delivery configuration to a deployed configuration. The bolt is adapted to be screwed onto a shank of the nut, so that the wire frames sealingly engage the vessel or tissue surrounding the puncture.

In accordance with one aspect of the present invention, the occlusion element of the second embodiment may be repositioned by configuring the bolt to be partially unscrewed from the nut.

In a third embodiment of the present invention, the occlusion element comprises a disk identical to that of the first embodiment, and a spring coupled thereto. Expansion of the spring from a contracted, equilibrium configuration, to a deployed configuration may be actuated by application of a proximal force to a string attached thereto. When the spring is deployed and engaged to tissue surrounding a puncture tract proximally coupled to the puncture, the disk is maintained in sealing engagement with the vessel or tissue disposed distal the puncture.

According to another aspect of the present invention, the occlusion elements may be made from a biodegradable polymer.

BRIEF DESCRIPTION OF THE DRAWINGS

Further features of the present invention, its nature and various advantages will be more apparent from the accompanying drawings and the following detailed description of the preferred embodiments, in which:

FIG. 13 are schematic side views of an exemplary method of using the occlusion element of FIGS. 11 and 12.

DETAILED DESCRIPTION OF THE PREFERRED EMBODIMENTS

The present invention relates to self-expanding occlusion elements that may be inserted to seal a vessel or tissue puncture by engaging the vessel or tissue surrounding the puncture. Furthermore, the apparatus of the present invention includes minimally invasive delivery elements that may be used to deliver the occlusion elements to the puncture site, and, optionally, to reposition the occlusion element after it has been engaged to the vessel or tissue surrounding the puncture. In particular, the following written description illustratively describes use of the apparatus of the present invention to close punctures in a vessel wall, wherein a representative puncture is disposed continuous with and distal to a puncture tract that is disposed through subcutaneous tissue and that proximally terminates at the skin of a patient. However, it will be evident to one of ordinary skill in the art that the present invention may be used to occlude any subcutaneous puncture through a vessel or tissue.

Figure 1:
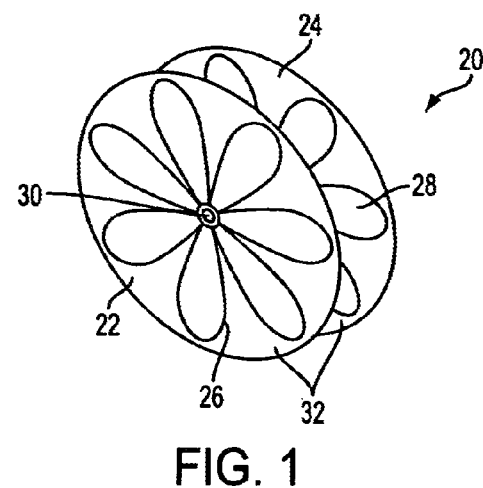
FIG. 1 is a schematic perspective view of an occlusion element of the present invention disposed to occlude a puncture.

Referring to FIG. 1, occlusion element 20 of the present invention is illustrated in its expanded configuration. Occlusion element 20 includes first disk 22 and second disk 24 respectively comprising first self-expanding wire frame 26 and second self-expanding wire frame 28. Wire frames 26 and 28 may be connected together via joint 30, e.g., a bead of solder, and optionally may be encased in a flexible, fluid impermeable membrane 32. When disposed in the expanded configuration, the diameters of disks 22 and 24 are greater than the diameter the puncture. Alternatively, membrane 32 may be omitted, and one or both of wire frames 26 and 28 may be coated with a coagulant-promoting coating, e.g., thrombin, fibrin or human factor VIII. As yet another alternative, frames 26 and 28 may be provided bare, without coatings or membranes.

Figure 2A:
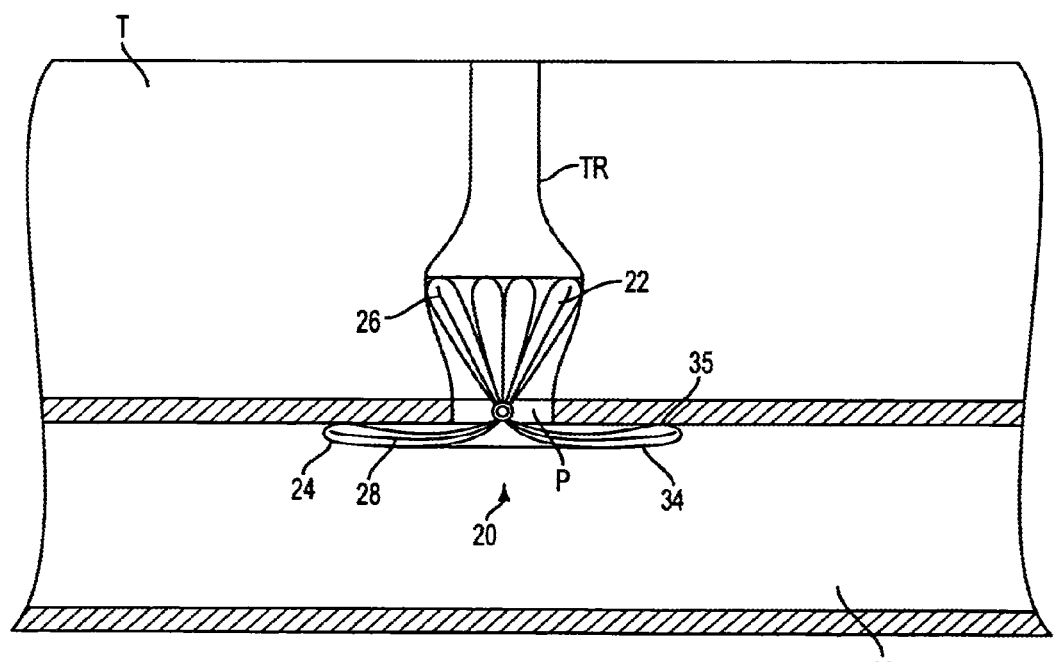
FIG. 2 are schematic cross-sectional views of the occlusion element of FIG. 1, disposed to occlude the puncture.

In the expanded, configuration shown in FIG. 2A, wire frame 28 is configured to expand so that disk 24 forms everted arc 34 that causes outer edge 35 of disk 24 to engage and compress against the interior wall of vessel V. For purposes of illustration, the depth of arc 34 relative to the diameter of vessel V is exaggerated in FIG. 2. Wire frame 26 preferably is biased to urge frame 26 towards wire frame 28. This biasing force causes disk 24 to sealingly engage the interior wall of vessel V to reduce blood leakage from vessel V. Due to the presence of tissue surrounding puncture tract TR, disk 22 may not fully expand into the configuration of FIG. 1. To enhance engagement of disk 22 with tissue T when it is expanded within the puncture tract, wire frame 26 optionally may include barbs, hooks, sharp edges, or roughened surfaces that can penetrate into tissue T and/or enhance resistance to migration of disk 22 within the puncture tract. Disk 24 may also include optional tissue engagement apparatus.

In a preferred embodiment, the depth of arcs 34 is shallow compared to the diameter-of vessel V. Thus, when device 20 is deployed against the vessel wall, disk 24 substantially conforms to the vessel's inner wall both in the longitudinal and circumferential directions, as will be discussed in greater detail hereinbelow, thereby reducing the risk that blood flow within the vessel will be disturbed.

In an alternative embodiment, shown in FIGS. 2B and 2C, occlusion element 20 comprises disks 36 and 38, that, when expanded, lie flush against tissue T surrounding puncture tract TR and the inner wall of vessel V, respectively. Accordingly, disk 38 substantially conforms to the profile of the inner wall of vessel V when engaged thereto. Disk 38 adopts the shape of an arcuate portion of a cylinder, or roughly the shape of a saddle. Accordingly, wire frame 38 preferably is sufficiently rigid to permit disk 24 to self-expand and engage the interior wall of vessel V, and sufficiently flexible to conform to the profile of the inner wall of vessel V. This further reduces the disturbance to blood flow within vessel V, and reduces the risk of thrombosis.

Like the disks of FIG. 2A, disks 36 and 38 also may be biased toward each other to sealingly engage disk 38 to the inner vessel wall when deployed. Moreover, because disk 38 is configured to substantially conform to the inner wall of vessel V, there is a greater contact area between disk 38 and vessel V than in the embodiment of FIG. 1, thereby enhancing resistance to migration. Optionally, to enhance engagement of disks 36 and 38 to tissue T and vessel V, respectively, the disks also may include barbs, hooks, sharp edges, or roughened surfaces that can penetrate into tissue T or vessel V, and/or enhance resistance to migration of disk 36 within puncture tract TR.

In a further alternative embodiment, shown in FIG. 2D, occlusion element 20 may comprise disk 22 disposed proximal to puncture P, and disk 38 that substantially conforms to the profile of the inner wall of vessel V when deployed. As in the preceding embodiments, disks 22 and 38 preferably are biased toward each other and optionally may comprise barbs, hooks, sharp edges, or roughened surfaces to enhance sealing engagement of the disks to the inner wall of vessel V or puncture tract TR.

Figure 3A:
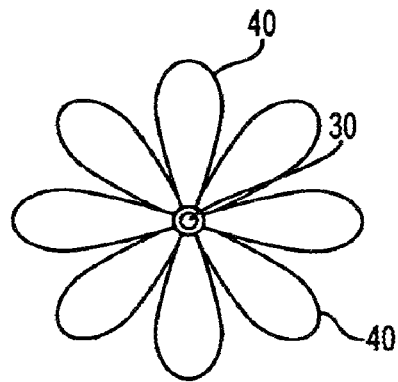
FIG. 3 are schematic plane views of wire frames of the occlusion element of FIGS. 1 and 2.
Figure 3B:
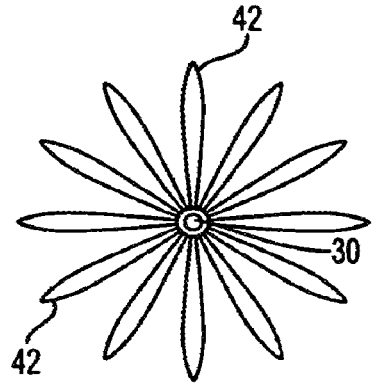

In a preferred embodiment of the present invention illustrated in FIG. 3A, wire frames 26 and 28 comprise plurality of petals 40 having rounded outer edges. Plurality of petals 40 may be formed from a single wire or a plurality of wires, wherein each petal may be joined to the remaining petals at joint 30. Alternatively, one or both of wire frames 26 and 28 may comprise plurality of petals 42 (see FIG. 3B), wherein each petal 42 is spicular in shape, having a slightly rounded outer edge to prevent trauma to tissue T and the vessel wall when engaged thereagainst. Alternatively, the outer edges of spicular petals 42 may be sharp, hooked or barbed so that they firmly engage the tissue and/or the vessel wall. Like petals 40, petals 42 may be formed from a single wire or a plurality of wires, wherein each petal may be joined to the remaining petals at joint 30.

In accordance with another aspect of the present invention, part or all of occlusion element 20 is manufactured from a biodegradable polymer, such as polyglycolic acid. This permits occlusion element 20 to be resorbed into and excreted from a patient's body after the puncture has healed. It will be evident to one of ordinary skill in the art that, by controlling parameters such as the degree of polymerization and crystallization, the biodegradable polymer may be engineered to comprise material properties that permit occlusion element 20 to self-expand from its delivery configuration, and to degrade at a predetermined rate.

Alternatively, occlusion element 20 may be manufactured from a non-biodegradable material. Specifically, the wire frames may comprise a material that may be elastically contracted from the expanded configuration of FIGS. 1-3 into the delivery configuration of FIG. 4. During delivery of occlusion element 20, the material also should permit occlusion element 20 to self-expand back into its expanded configuration irrespective of the ambient temperature to which it is exposed. Suitable materials may comprise a flexible biocompatible metal such as spring steel, stainless steel or a nickel titanium alloy.

In accordance with yet another aspect of the present invention, membrane 32 of occlusion element 20 may be omitted and one or both wire frames 26 and 28 may be coated with coagulant-enhancing agents, such as thrombin, fibrin or human factor VIII, to accelerate the sealing process. As a further alternative, such agents may be applied to membrane 32, if present. As yet another alternative, frames 26 and 28 may be provided bare, having no membrane or coagulant-enhancing agent.

Figure 4:
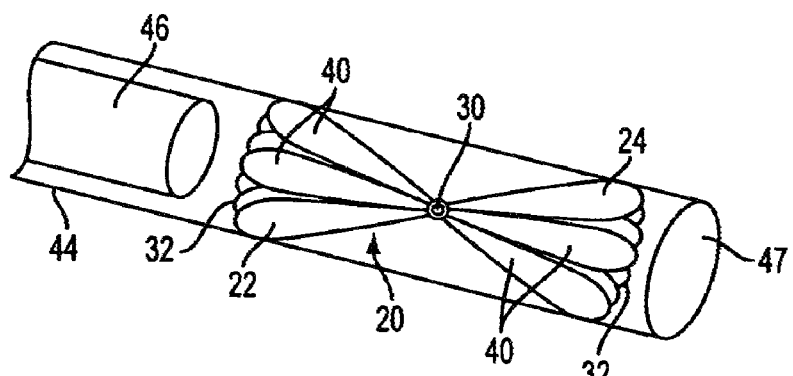
FIG. 4 is a schematic perspective view of the occlusion element of FIGS. 1-3 in its contracted delivery configuration, disposed within a delivery sheath.

Referring now to FIG. 4, occlusion element 20 is shown disposed within minimally invasive delivery sheath 44, folded into-its delivery configuration in which petals 40 are aligned with the longitudinal axis of sheath 44, and membrane 32, if present, is furled therein. Push rod 46 may be inserted proximal to occlusion element 20 within sheath 44, with a proximal end of the push rod extending out of the patient so that a medical practitioner may use push rod 46 to urge occlusion element 20 through sheath 44 towards distal opening 47 for delivery to puncture P.

Referring to FIG. 5, an exemplary method of using occlusion element 20 of the present invention is described. Delivery sheath 44, which may comprise a catheter that had been used in a preceding minimally invasive diagnostic or therapeutic procedure, is inserted into puncture tract TR. Sheath 44 may comprise a material typically used for vascular sheaths, such as polyethylene or nylon, and comprises distal opening 47 and central lumen 48 through which minimally invasive diagnostic or therapeutic devices may be advanced to perform the previous diagnostic or therapeutic procedure. Example procedures include but are not limited to angioplasty, angiography, atherectomy, and vascular stenting. Sheath 44 also may comprise a radiopaque marker (not shown) disposed adjacent distal opening 47 to facilitate disposition of sheath 44 within puncture tract TR and vessel V.

Figure 5A:
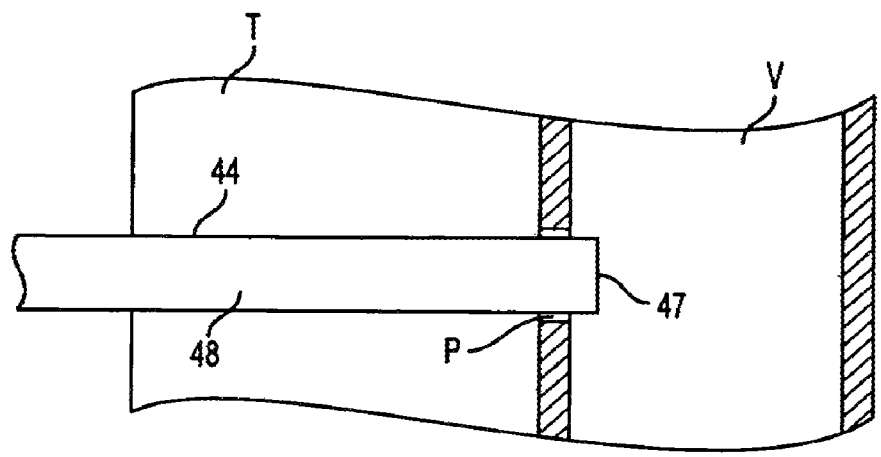
FIG. 5 are schematic side views of an exemplary method of using the occlusion element of FIGS. 1-4.

Alternatively, sheath 44 may be introduced within puncture tract TR and disposed across puncture P as shown in FIG. 5A, immediately preceding the present procedure.

Figure 5B:
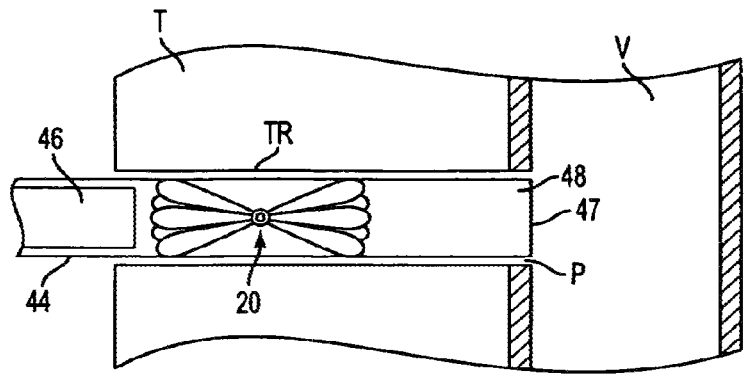

As seen in FIG. 5B, once sheath 44 is properly positioned across and slightly distal puncture P, occlusion element 20 is loaded into the proximal end of lumen 48 of sheath 44 located outside the patient. Push rod 46 is inserted thereafter. As will be apparent to those of skill in the art, occlusion element 20, as well as push rod 46, alternatively may be loaded within lumen 48 of sheath 44 prior to placement of sheath 44 across puncture P.

Figure 5C:
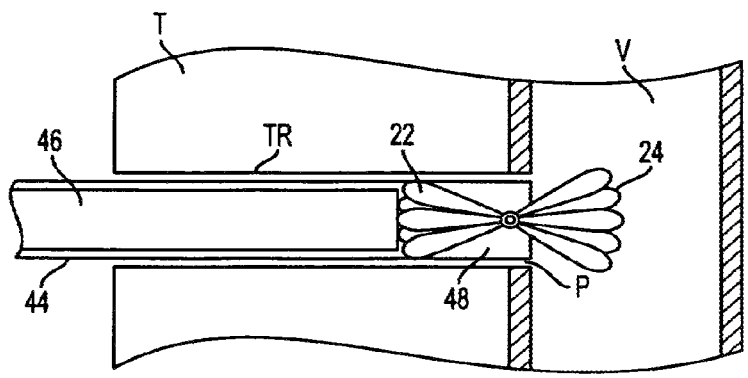

Axial force is applied to push rod 46 in the distal direction to urge occlusion element 20 through lumen 48 towards distal opening 47. Additional force applied to push rod 46 in the axial direction advances occlusion element 20 past distal opening 47 of sheath 44. Once extended beyond the distal end of sheath 44, disk 24 self-expands and unfurls within the lumen of vessel V, as seen in FIG. 5C.

Figure 5D:
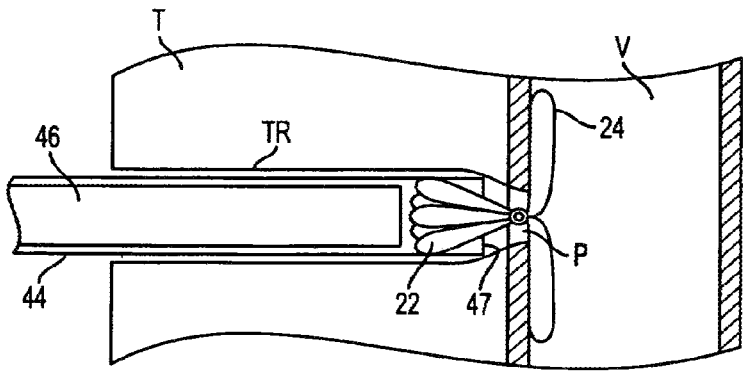
Figure 5E:
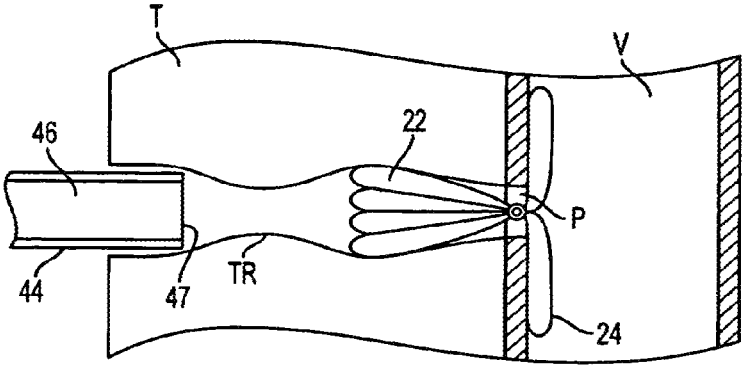

Sheath 44 and push rod 46 then are proximally retracted with respect to puncture P to urge disk 24 into sealing engagement with the interior wall of vessel V, as seen in FIG. 5D. Once a medical practitioner feels resistance caused by such engagement, push rod 46 is held stationary while sheath 44 is continually retracted to urge the remainder of occlusion element 20 past distal opening 47 of sheath 44. Upon exiting sheath 44, disk 22 self-expands proximal to puncture P within puncture tract TR, and engages tissue T surrounding the puncture tract. Due to the bias of disks 22 and 24 toward each other, as well as optional barbs, hooks, sharp edges, or roughened surfaces disposed thereon that enhance resistance to migration of the disks, disk 24 is maintained in sealing engagement against the interior wall of vessel V. In this manner, occlusion element 20 seals puncture P and prevents blood from leaking out of vessel V.

As an-alternative delivery method, sheath 44 and push rod 46 may once again be retracted proximally until disk 24 engages the interior wall of vessel V, as in FIG. 5D. The medical practitioner may then continue to proximally retract sheath 44 and push rod 46. Resistance applied by the interior wall of vessel V to retraction of disk 24 of occlusion element 20 is expected to pull disk 22 out of lumen 48 and fully deploy occlusion element 20 into contact with tissue T and the interior wall of vessel V, as in FIG. 5E. Such resistance may be magnified, for example, by placing optional barbs, hooks, roughened surfaces or sharp edges at the periphery of disk 24 such that the disk is affixed to the interior vessel wall. In effect, once disk 24 has been unfurled within the lumen of vessel V, the medical practitioner need only retract sheath 44 and push rod 46 to fully deploy occlusion element 20.

Figure 6A:
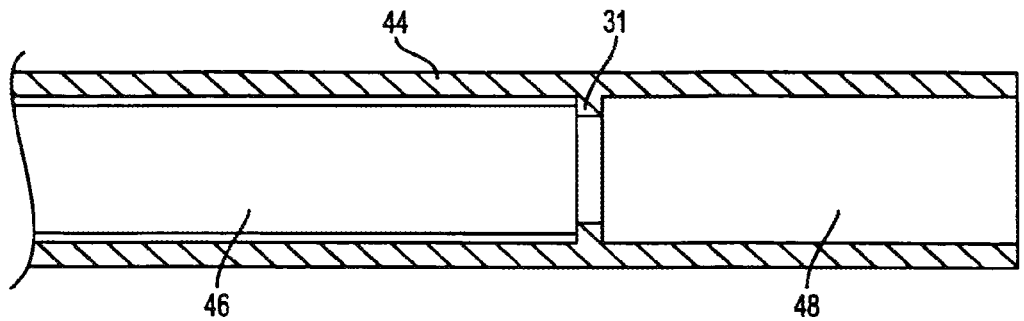
FIG. 6 are schematic views of delivery elements that may be used to deliver the occlusion element of the present invention.

It should be understood that sheath 44 and/or push rod 46 may be provided with apparatus for limiting a maximum distal depth to which push rod 46 may be inserted into lumen 48 of sheath 44. As illustrated in FIG. 6A, for example, lumen 48 may comprise step or narrowing 31 in its distal region to limit insertion of push rod 46 to the maximum distal depth. Such depth may be chosen, for example, such that push rod 46 may advance disk 24 of occlusion element 20 out of distal opening 47 of sheath 44, but may not advance disk 22 out of opening 47. As will be apparent, step or narrowing 31 may be localized, as in FIG. 6A, or may extend along a portion of sheath 44, for example, the remainder of sheath 44 disposed distal of step or narrowing 31.

As yet another alternative, push rod 46 and lumen 44 may be keyed such that push rod 46 may be advanced to a first maximum distal depth within sheath 44 in a first configuration, and a second maximum distal depth within sheath 44 in a second configuration. The first maximum depth may be provided, for example, such that disk 24 of occlusion element 20 may be advanced out of distal opening 47, while the second maximum depth may be provided such that disk 22 may be advanced out of opening 47. Push rod 46 and sheath 44 may be transferred from the first configuration to the second configuration, for example, by rotating the push rod and/or the sheath with respect to one another.

Figure 6B:
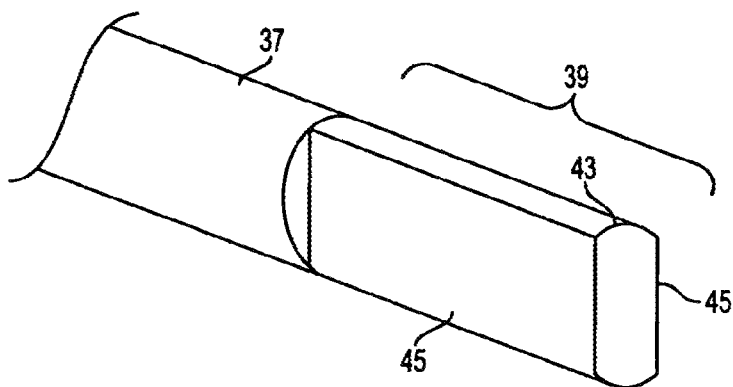
Figure 6C:
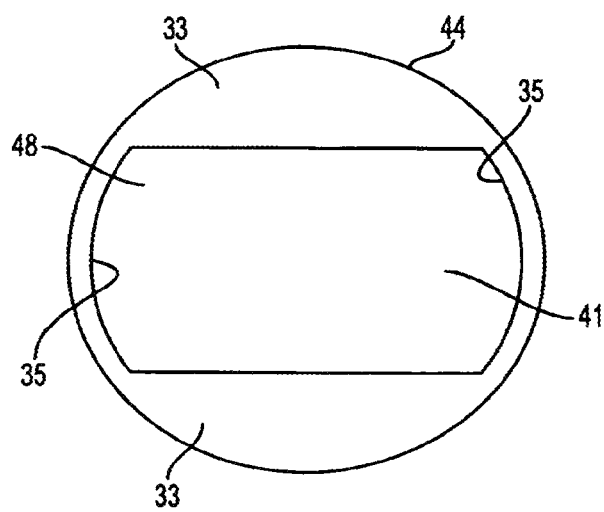

An example of such selective motion constraint is provided in FIGS. 6B-6C. Sheath 44 may be provided with partial step or narrowing 33 that extends around only a portion of interior surface 35 of the sheath at the first maximum depth. Push rod 37 may, in turn, be provided with distal portion 39 that has a cross-sectional profile that matches opening 41 defined by partial step or narrowing 33 and interior surface 35. In the example shown in FIG. 6B, push rod 37 has opposing cylindrical surfaces 43 that match the curvature of interior surface 35 and are connected by opposing planar surfaces 45. When limited to the first maximum depth, push rod 37 is rotationally positioned so that distal portion 39 abuts partial step or narrowing 33 of lumen 48. Rotating the push rod with respect to the sheath then may align distal portion 39 of the push rod with opening 41 so that planar surfaces 45 are aligned with partial step 33 in lumen 48, and cylindrical surfaces 43 are aligned with interior surfaces 35. This configuration permits push rod 37 to be further advanced within lumen 48 until partial step 33 contacts ledge 49 of push rod 46. In this axial position, push rod 37 has fully deployed occlusion element 20 from sheath 44.

Additional techniques for achieving selective motion constraint will be apparent to those of skill in the art. For example, push rod 46 and sheath 44 may engage one another in a corkscrew fashion at the first maximum distal depth, such that rotation of push rod 46 with respect to sheath 44 while sheath 44 is held stationary may cause distal advancement of the rod to the second maximum depth within lumen 48.

Figure 7:
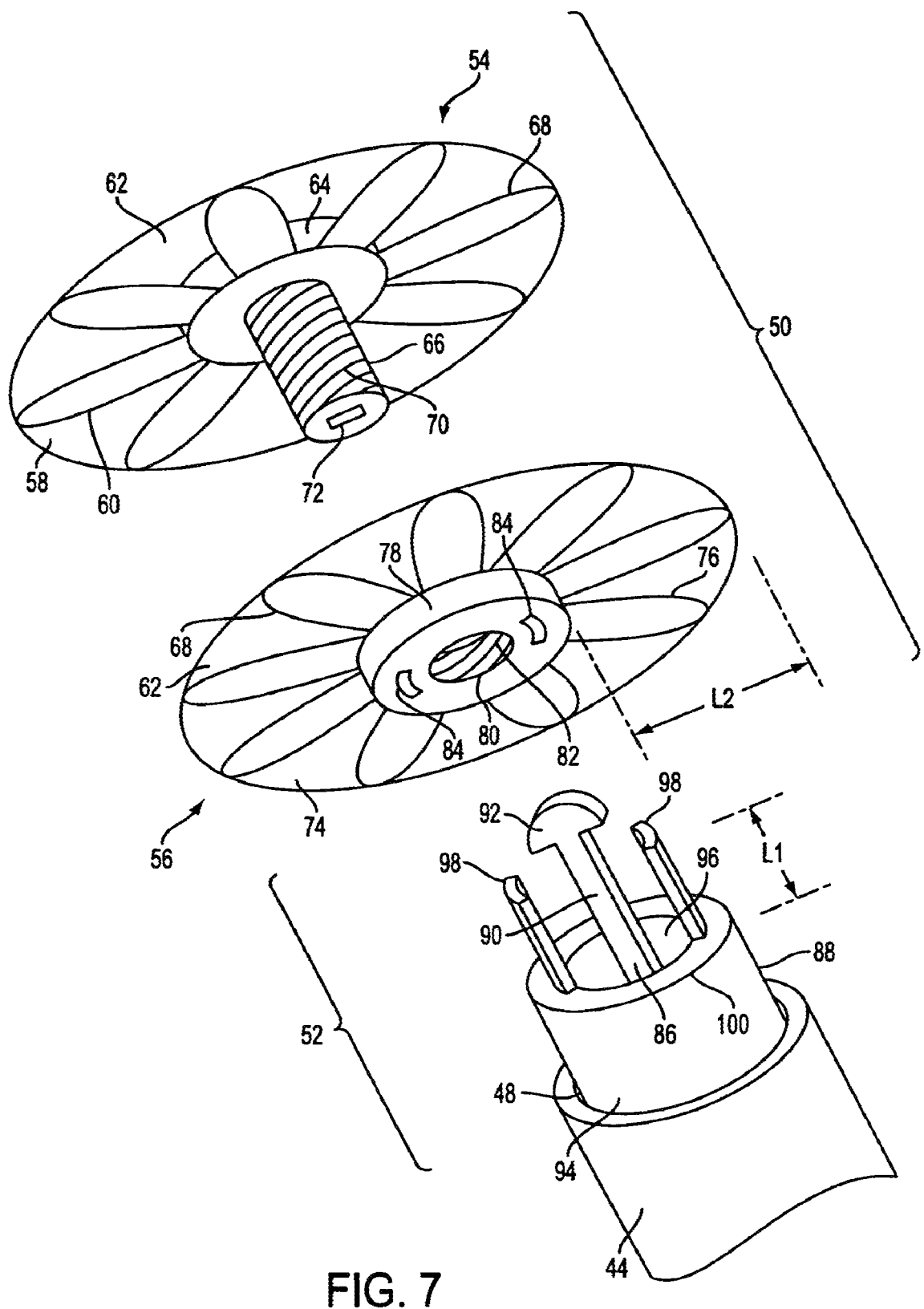
FIG. 7 is a schematic perspective view of a second embodiment of the occlusion element of the present invention, and delivery shafts that facilitate use of the occlusion element.

Referring now to FIG. 7, an alternative embodiment of the present invention is described in which occlusion element 50 may be repositioned without inflicting additional trauma to the vessel wall to which it is engaged. This alternative embodiment comprises occlusion element 50, and minimally invasive delivery shafts 52 disposed within sheath 44. Occlusion element 50 includes bolt 54 and nut 56, which is configured to be screwed onto bolt 54 to engage tissue T and the wall of vessel V interposed therebetween. Bolt 54 comprises first disk 58 having self-expanding wire frame 60 optionally encased by flexible fluid-impermeable membrane 62, head 64, and shank 66. Wire frame 60 comprises plurality of petals 68, and may be either integrally manufactured with or molded into head 64. Shank 66 projects out of and may be integral with head 64, and includes threads 70 and keyhole 72, which will be described in greater detail below.

Nut 56 comprises second disk 74 having self-expanding wire frame 76 optionally encased by flexible fluid-impermeable membrane 62, and nut element 78. Wire frame 76 comprises plurality of petals 68, and may be either integrally manufactured with or molded into nut element 78. Nut element 78 also comprises bore 80 having threads 82 adapted to engage threads 70 of bolt 54, and blind slots 84 that may be used in a manner described in greater detail below to facilitate engagement of nut 56 to bolt 54.

It will be obvious to one of ordinary skill in the art that first and second disks 58 and 74 may be configured to self-expand into any of the profiles illustrated in FIGS. 2A-2C. Likewise, each petal 68 also may comprise rounded outer edges as illustrated in FIG. 3A, or the spicular shape shown in FIG. 3B. Additionally, membranes 62 optionally may be omitted and wire frames 60 and 76 provided either bare or coated with coagulant-enhancing agents, such as thrombin, fibrin or human factor VIII, to accelerate the sealing process.

As with occlusion element 20, bolt 54 and nut 56 may be manufactured from a biodegradable material, such as polyglycolic acid, that may be engineered to permit occlusion element 50 to self-expand into its deployed configuration from a retracted delivery configuration, and to degrade at a predetermined rate. Alternatively, occlusion element 50 may comprise a non-biodegradable material, for example, a flexible biocompatible metal such as a spring steel, a stainless steel or a nickel titanium alloy. Wire frames 60 and 76 preferably comprise a material that may be elastically contracted from the expanded configuration of FIG. 7 into the delivery configuration of FIGS. 10A and 10B. During delivery of occlusion element 50, the material also preferably permits occlusion element 50 to self-expand back into its expanded configuration irrespective of the ambient temperature to which it is exposed.

Still referring to FIG. 7, delivery shafts 52 comprise independently actuable shafts 86 and 88, which are adapted to be translatably disposed within sheath 44. Shaft 86 comprises bar 90 and key 92. Proximally extending out of the patient, bar 90 may be longitudinally actuated and rotated to engage key 92 with keyhole 72 of bolt 54 to facilitate longitudinal advancement of occlusion element 50 and engagement of nut 56 to bolt 54 in a manner described in greater detail hereinbelow.

Concentrically disposed within sheath 44, shaft 88 comprises cylindrical body 94 having lumen 96 sized to permit longitudinal advancement and rotation of shaft 86 therein. Shaft 88 proximally extends out of the patient and may comprise a handle (not shown) at the proximal end to facilitate rotation thereof. In a preferred embodiment, the outer diameter of cylindrical body 94 of shaft 88 may be dimensioned to approximately equal the diameter of lumen 48 of sheath 44.

Projecting from the distal end of body 94 are prongs 98 that are configured to engage blind slots 84 disposed within nut element 78. Prongs 98 comprise a longitudinal length L1 that is approximately equal to the sum of length L2 of petals 68 and the depth of blind slots 84. Prongs 98 also are inset from edge 100 of cylindrical body 94 so that second disk 74 may be furled and disposed within lumen 48 in an annular space between prongs 98 and sheath 44 when second disk 74 is in its delivery configuration (see FIGS. 10A-10B). While FIG. 7 illustratively depicts only two pairs of prongs 98 and blind slots 84, additional prongs 98 and slots 84 may be incorporated to distribute shearing forces generated when shaft 88 is engaged to slots 84 and rotated to screw nut 56 onto shank 66 of bolt 54.

Figure 8A:
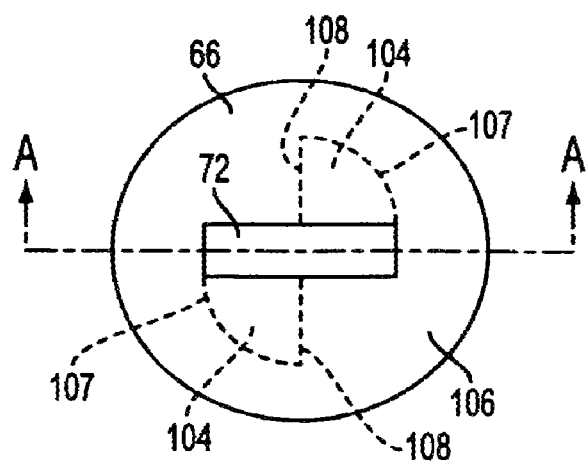
FIG. 8 are schematic close up views of a shank of a bolt of the occlusion element of FIG. 7.
Figure 8B:
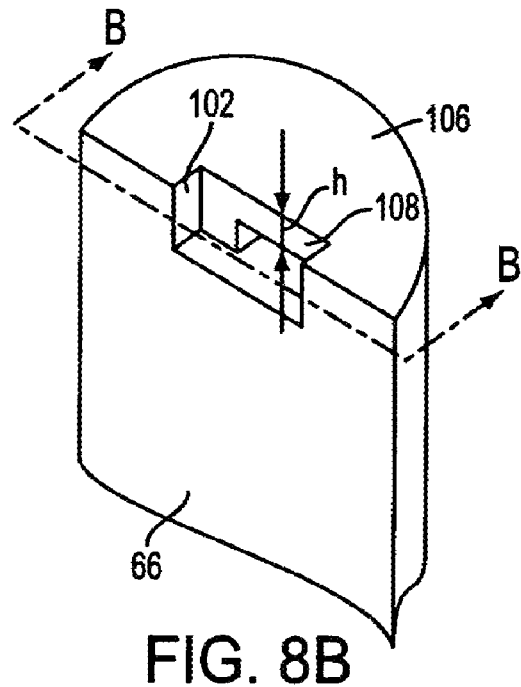
Figure 8C:
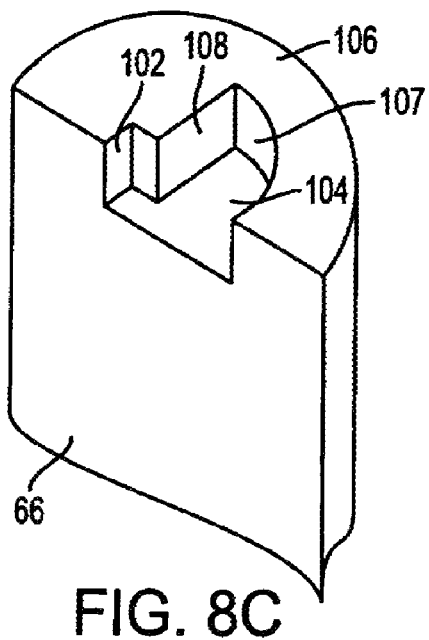

Referring now to FIG. 8, shank 66 and keyhole 72 are described in greater detail. In a preferred embodiment of the present invention, shank 66 comprises keyhole 72 disposed at the opening to entrance chamber 102, and chambers 104 that are disposed in communication with entrance chamber 102. Chambers 104 are separated from proximal surface 106 of shank 66 by portion 108 having thickness h. Thickness h may be chosen so that chambers 104 are disposed near the proximal end of shank 66, near the distal end of head 64, or anywhere therebetween. Portion 108 facilitates delivery of occlusion element 50 by preventing disengagement of key 92 from bolt 54 under the force of gravity, and may be used to transmit proximally directed force applied to shaft 86 to bolt 54.

Each chamber 104 is configured to permit key 92 of shaft 86 to be rotated therein after insertion into entrance chamber 102 through keyhole 72, thereby locking key 92 to bolt 54. Specifically, each chamber 104 comprises lateral wall 107 that is curved in a circular arc, and stop wall 108 that prevents further rotation of shaft 86.

Figure 9A:
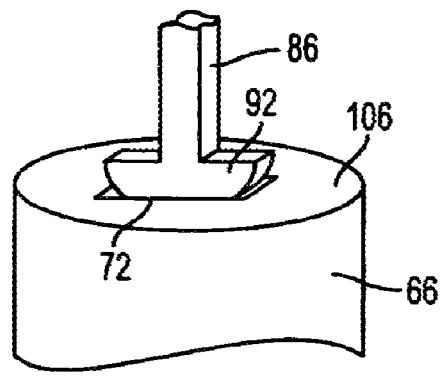
FIG. 9 are schematic perspective views of an exemplary method of engaging a delivery shaft of FIG. 7 to the shank of the bolt of the occlusion element of FIGS. 7 and 8.
Figure 9B:
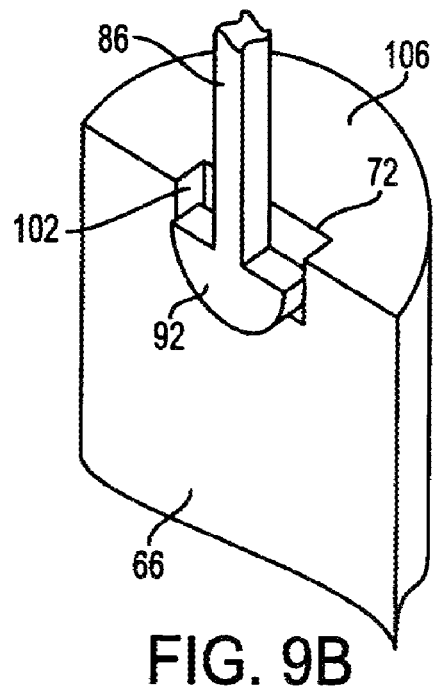

In operation, as illustrated in FIG. 9, key 92 may be preloaded into entrance chamber 102 through keyhole 72 prior to insertion of occlusion element 50 into delivery sheath 44, which may be disposed within the patient through puncture tract TR and puncture P. Occlusion element 50, as well as its associated delivery system, alternatively may be inserted into delivery sheath 44 prior to advancement of the delivery sheath into a patient's vessel. After insertion of key 92 into entrance chamber 102, shaft 86 is rotated, for example in the counterclockwise CCW direction, so that key 92 enters chambers 104, rotating about centerline CL of the circular arcs of lateral walls 107. Rotation ceases when key 92 abuts stop walls 108.

In this position, any movement of shaft 86, except counterrotation, for example, in the clockwise CW direction, will transmit movement to bolt 54. In particular, application of distal force along the longitudinal axis of shaft 86 advances bolt 54 in the distal direction, whereas application of proximal force pulls bolt 54 in the proximal direction. Furthermore, lateral movement of shaft 86 transmits force to one or more of lateral walls 107 and/or stop walls 108, translating bolt 54 therewith, and thereby providing greater control in the disposition of bolt 54.

As will be apparent to those of skill in the art, shaft 86, or other portions of the delivery apparatus or occlusion device, optionally may comprise a safety lock (not shown) capable of limiting or halting counter-rotation of shaft 86 with respect to keyhole 72 of shank 66 when key 92 abuts stop walls 108. Once the safety lock has been deactivated, shaft 86 may again be counter-rotated with respect to keyhole 72. In this manner, a risk of accidental disengagement of key 92 from shank 66 may be reduced.

In a preferred embodiment of the present invention, in addition to key 92 being preloaded into chambers 104, occlusion element 50 may be inserted into sheath 44 with nut element 78 of nut 56 partially threaded onto shank 66 of bolt 54. Consequently, when shaft 86 is actuated to direct disposition of bolt 54 with respect to puncture P, nut 56 also may be positioned therewith. Furthermore, threads 70 of bolt 54 and threads 82 of nut 56 may be connected in such a manner that bolt 54 and nut 56 may not be completely detached from one another, thereby reducing a risk of accidental detachment of the nut from the bolt when the bolt is disposed within a patient's blood vessel. For example, once bolt 54 and nut 56 are threaded together, the terminus of either threads 82 or threads 70 may be deformed so that the bolt and the nut may not be fully removed from one another, while still allowing the distance between the nut and bolt to be altered. Alternatively, the terminus of threads 70 and 82 may comprise a one-way valve that allows the nut and bolt to be threaded together, but not completely unscrewed. Additional techniques will be apparent to those of skill in the art.

With reference to FIG. 10, an exemplary method of using occlusion element 50 of the present invention is described. As discussed with reference to FIG. 5A, sheath 44 shown in FIG. 10A may comprise a catheter that had been used in a previous minimally invasive diagnostic or therapeutic procedure, or a sheath newly inserted through puncture tract TR to deliver occlusion element 50 of the present invention. Prior to insertion of occlusion element 50 into lumen 48 of delivery sheath 44, nut 56 and shaft 86 preferably are at least partially engaged to bolt 54 in the manner described hereinabove. If nut element 78 is partially threaded onto shank 66, a sufficient distance must be maintained between bolt 54 and nut 56 to enable deployment of bolt 54 distal to and nut 56 proximal to puncture P.

Figure 10A:
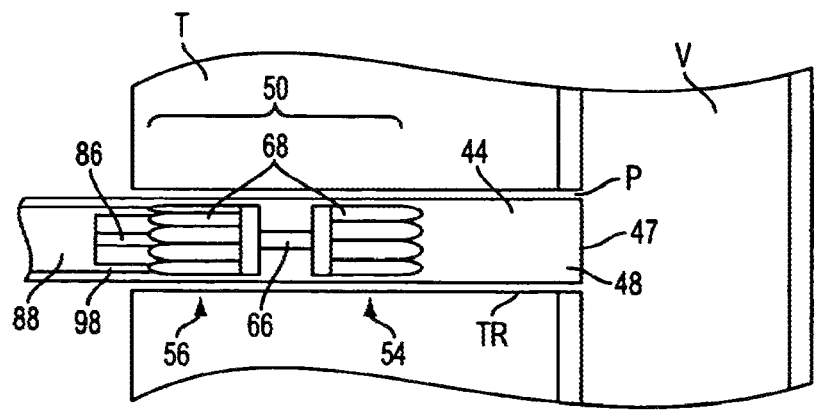
FIG. 10 are schematic side views of an exemplary method of using the occlusion element and delivery shafts of FIGS. 7-9.

As one unit, bolt 54, nut 56 and shaft 86 may be inserted into lumen 48 of sheath 44. Preferably, shaft 88 concurrently may be inserted therewith. After insertion, a distally-directed longitudinal force may be applied to shaft 86 to advance bolt 54 through lumen 48 towards puncture P. Since nut element 78 is partially threaded onto shank 66, distal advancement of bolt 54 also advances nut 56 therewith. As shown in FIG. 10A, plurality of petals 68 are aligned with the longitudinal axis of sheath 44 when occlusion device 50 is disposed in its delivery configuration.

Figure 10B:
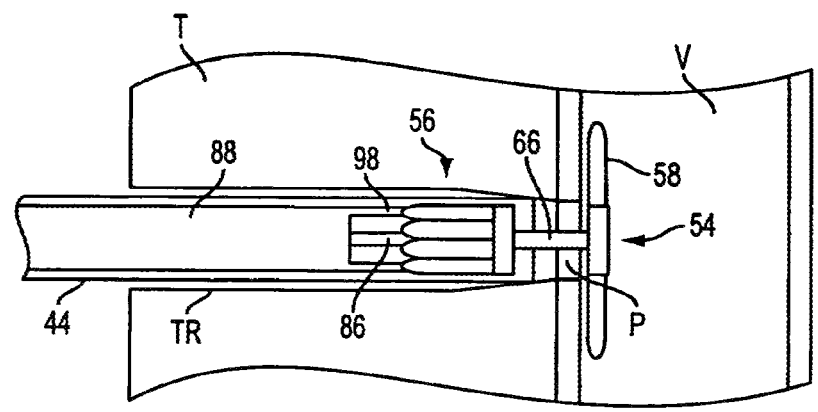
Figure 10C:
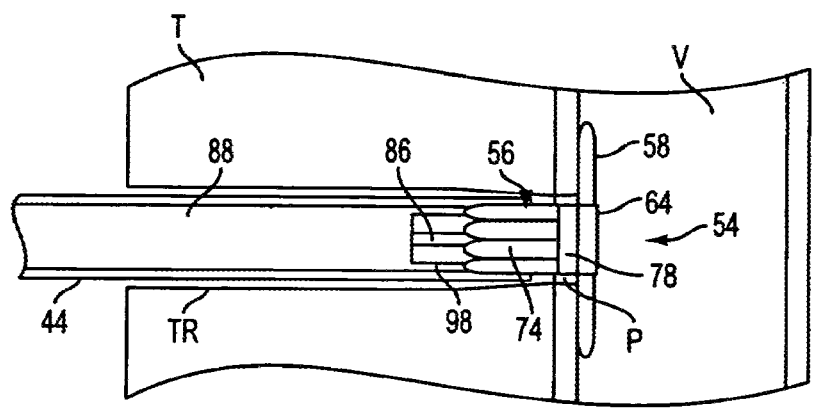
Figure 10D:
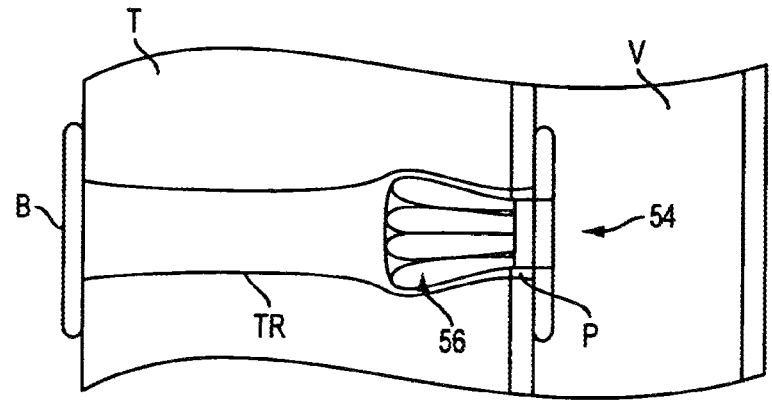

Once bolt 54 is advanced past distal opening 47 of sheath 44, first disk 58 self-expands from its contracted, delivery configuration to the expanded, deployed configuration, as seen in FIGS. 7 and 10B. To provide immediate hemostasis of puncture P, a proximally-directed force may be applied to shaft 86 to sealingly engage and substantially conform disk 58 to the inner wall of vessel V. If prongs 98 previously have not been engaged to blind slots 84, they may be engaged at this time by distally advancing and rotating shaft 88 until prongs 98 engage blind slots 84 disposed on nut element 78 (see FIG. 7).

Once prongs 98 are engaged with blind slots 84, further rotation of shaft 88, for example, in the clockwise CW direction, relative to shaft 86 advances nut 56 in the distal direction. Contemporaneously, contact of key 92 with stop walls 108 of chambers 104 prevents bolt 54 from rotating with nut 56 (see FIG. 8), and a proximally applied force to shaft 86 maintains disk 58 in sealing engagement and substantial conformity with the inner wall of vessel V. Rotation of shaft 88 continues until nut element 78 contacts head 64 of bolt 54. This may be determined by an increase in resistance to further rotation of shaft 88.

Figure 9C:
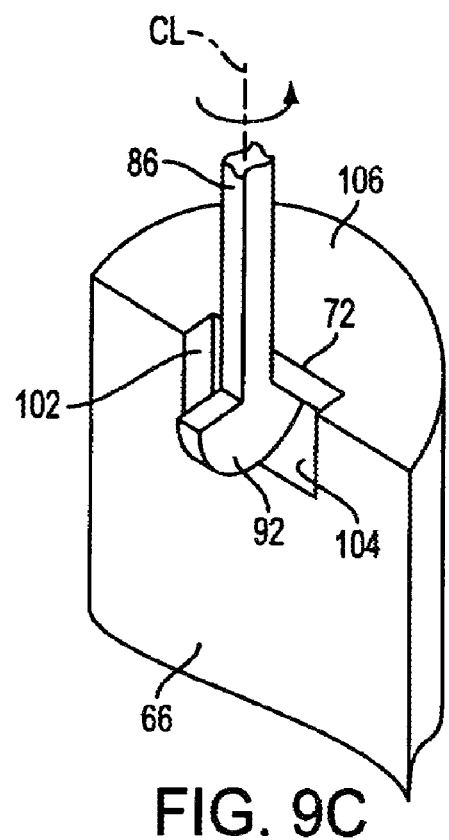

Sheath 44 then may be proximally retracted to permit disk 74 of nut 56 to be released from sheath 44 proximal to puncture P, and self-expand from its furled delivery configuration. Due to the presence of tissue T surrounding puncture tract TR, disk 74 does not fully expand into the configuration of FIG. 7, as shown in FIG. 9C. To enhance engagement of disk 74 with tissue T when it is expanded within the puncture tract, disk 74 optionally may include barbs, hooks, sharp edges, or roughened surfaces that can penetrate into the tissue and/or enhance resistance to migration of disk 74 within puncture tract TR. In this manner, occlusion element 50 may be disposed to engage tissue T and the interior wall of vessel V between bolt 54 and nut 56 to stop or reduce blood leakage from vessel V. Once occlusion element 50 has been delivered, shaft 86 and shaft 88 may be disengaged from occlusion element 50, for example, by counter-rotation of key 92, and proximally retracted with sheath 44 out of the patient. Bandage B may be affixed over the proximal opening to puncture tract TR to prevent contamination of the wound.

As discussed previously, in a preferred embodiment of the present invention, occlusion element 50 may be made of a biodegradable material. Accordingly, once puncture P has healed, occlusion element 50 may be resorbed and excreted by the patient's body, leaving behind little or no foreign matter at the puncture site.

Pursuant to another exemplary method of using the apparatus of the present invention, a medical practitioner may release occlusion element 50 from sealing engagement with the interior wall of vessel V, and reposition occlusion element 50 if it is determined that occlusion element 50 has been inappropriately disposed with respect to puncture P, or to remove occlusion element 50 for re-intervention within vessel V through puncture P. This may be easily accomplished by re-engaging occlusion element 50 with shafts 86 and 88, and rotating shank 66 of bolt 54 relative to nut 56, for example, in the clockwise CW direction. This releases occlusion element 50 from sealing engagement with the inner wall of vessel V, permitting occlusion element 50 to be repositioned or removed with respect to puncture P without abrading or otherwise damaging the vessel wall.

Occlusion element 50 may be repositioned by moving shaft 86, which is engaged to bolt 54. Since nut element 78 of nut 56 is partially threaded onto shank 66 of bolt 54, it too is repositioned with bolt 54. Re-engagement with the interior wall of vessel V may be re-established in the manner described hereinabove with reference to FIG. 10 once occlusion element 50 is properly positioned. In this manner, occlusion element 50 may be repositioned with respect to puncture P, even after occlusion element 50 has been deployed to sealingly engage the inner wall of vessel V and thereby seal puncture P. Alternatively, once occlusion element 50 has been disengaged, it may be retracted within sheath 44 by retracting shaft 86.

Figure 11:
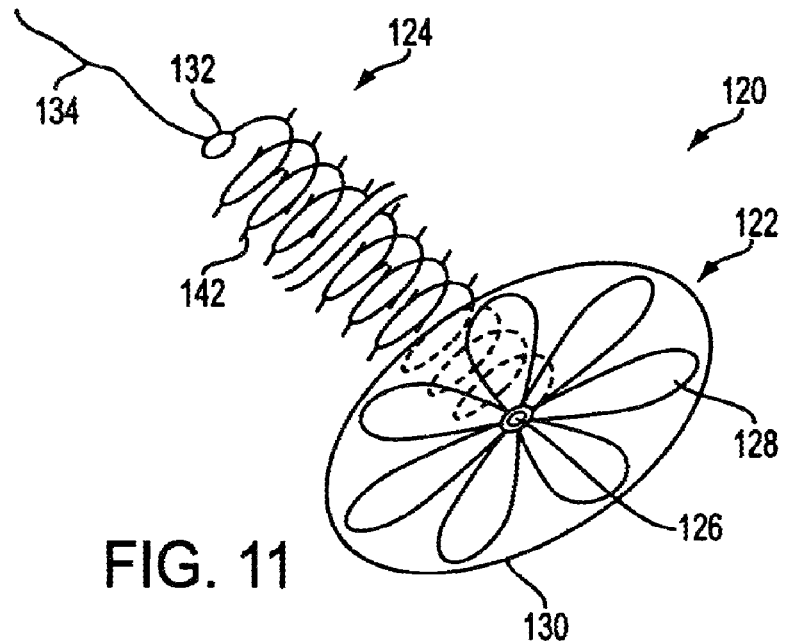
FIG. 11 is a schematic perspective view of a third embodiment of the present invention in its expanded configuration.
Figure 12:
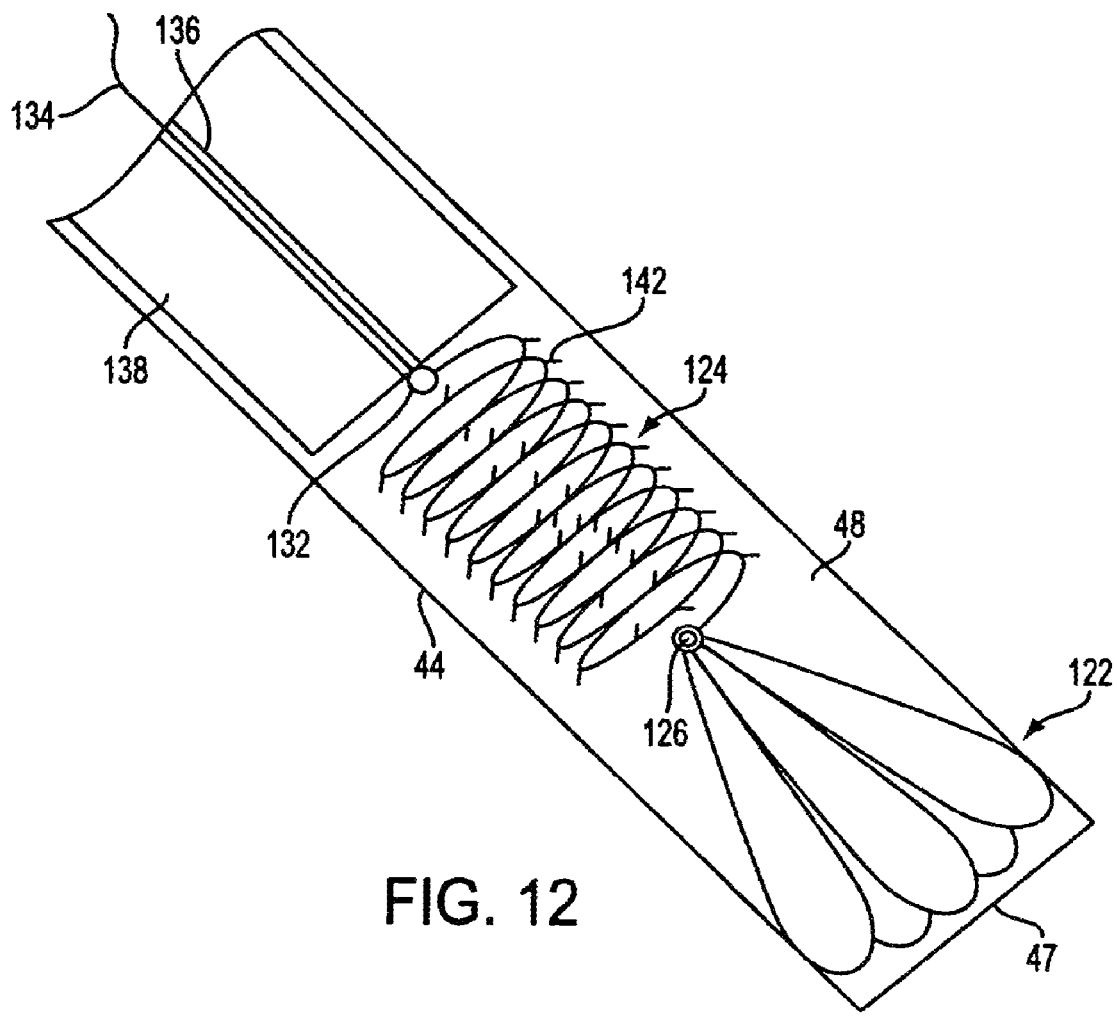
FIG. 12 is a schematic perspective view of the occlusion element of FIG. 11 in its contracted delivery configuration, disposed within a delivery sheath.

Referring now to FIGS. 11 and 12, a second alternative embodiment of the present invention is described. Occlusion element 120 includes self-expanding disk 122, joined to spring 124 via joint 126, e.g., a bead of solder. Similar to disk 24 or 38 of FIGS. 1-2, disk 122 substantially conforms to the inner vessel wall in both the longitudinal and circumferential directions when deployed thereagainst. Disk 122 incorporates wire frame 128, having a plurality of petals or spicules, as in FIG. 3.

Wire frame 128 provides disk 122 with sufficient rigidity to permit disk 122 to self-expand from its contracted, delivery configuration and sealingly engage the interior wall of vessel V, and sufficient flexibility to conform to the profile of the inner wall of vessel V. In its contracted delivery configuration shown in FIG. 12, wire frame 128 is elastically deformed to align with the longitudinal axis of delivery sheath 44. Wire frame 128 may be encased in flexible, fluid impermeable membrane 130, or coated with a coagulant-enhancing coating, e.g., thrombin, fibrin or human factor VIII. As yet another alternative, wire frame 128 may be provided bare without a membrane or coating. Furthermore, like the preceding embodiments, wire frame 128 may include sharp edges, barbs or hooks to firmly engage disk 122 to the interior wall of vessel V when deployed thereagainst.

Attached to disk 122 is spring 124, preferably consisting of a spring that resists expansion, e.g. a tension spring that is configured to engage tissue surrounding puncture tract TR to maintain disk 122 in sealing engagement and substantial conformity with the inner wall of vessel V. The force applied by a spring is typically defined by Hooke's law, where $F=-kx$, where F is the applied force, k is the spring constant, and x is the displacement of the spring from equilibrium. Spring constant k has units of force/unit length, and advantageously may be specified to controllably determine the force required to expand spring 124, as well as the restoring force applied by spring 124 after expansion. Thus, the spring constant may be tailored for use in specific clinical indications and/or with specific patient populations. Illustrative spring constants may range, for example, between 0.1 and 100. Additional spring constants will be apparent to those of skill in the art. Furthermore, nonlinear springs may be provided where $F=-kx^P$, where P represents a nonlinear exponent.

On the proximal end of spring 124 is eyelet 132 through which-string 134 may be threaded. String 134 may comprise, for example, a length of biodegradable suture. During delivery of occlusion element 120, string 134 is used to longitudinally expand spring 124 from its contracted, equilibrium configuration shown in FIG. 12 to an expanded configuration shown in FIG. 11. In the delivery configuration of FIG. 12, string 134 is disposed through lumen 136 of push rod 138, which is disposed proximal to occlusion element 120 within delivery sheath 44. String 134 is affixed to the proximal end of push rod 138 (not shown) so that a medical practitioner may access and release string 134 therefrom. Spring 124 may include optional barbs, hooks, roughed surfaces, or sharp edges 142 to enhance engagement with tissue T surrounding puncture tract TR.

In a preferred embodiment, occlusion element 120 may be manufactured from a biodegradable material, such as polyglycolic acid, that may be engineered to permit occlusion element 120 to expand into its deployed configuration from its retracted delivery configuration, and to degrade at a predetermined rate. Alternatively, occlusion element 120 may comprise a non-biodegradable material, for example, a flexible biocompatible metal such as a spring steel, a stainless steel or a nickel titanium alloy. Wire frame 128 preferably is made of a material that may be elastically contracted from the expanded configuration of FIG. 11 into the delivery configuration of FIG. 12. During delivery of occlusion element 120, the material preferably also permits occlusion element 120 to expand back into its expanded configuration irrespective of the ambient temperature to which it is exposed.

Referring now to FIG. 13, an exemplary method of using occlusion element 120 is described. As discussed previously, sheath 44 shown in FIG. 13A may comprise a catheter that had been used in a previous minimally invasive diagnostic or therapeutic procedure, or a sheath newly inserted through puncture tract TR and puncture P to deliver occlusion element 120. Once sheath 44 is properly positioned across and slightly distal to puncture P, occlusion element 120 is loaded into the proximal end of lumen 48 of sheath 44 located outside the patient, with thread 134 affixed to eyelet 132 and disposed through lumen 136 of push rod 138. Push rod 138 is inserted thereafter. As will be apparent to those of ordinary skill in the art, occlusion element 120, as well as push rod 138, may be pre-loaded into sheath 44 prior to insertion of sheath 44 into puncture tract TR.

Axial force is applied to push rod 138 in the distal direction to urge occlusion element 120 through lumen 48 towards distal opening 47 of sheath 44. Additional force applied to push rod 138 in the axial direction advances occlusion element 120 past distal opening 47, at which point disk 122 self-expands and unfurls within the lumen of vessel V. Sheath 44 then is proximally retracted from puncture P, along with push rod 138. Proximal retraction of sheath 44 and push rod 138 ceases when disk 122 engages the inner wall of vessel V, which may be determined by an increase in resistance to continual proximal retraction thereof. This sealingly engages and substantially conforms disk 122 to the vessel's inner wall, thereby providing immediate hemostasis.

With sheath 44 held stationary within puncture tract TR just proximal to puncture P, push rod 138 is continually retracted in the proximal direction along with string 134 affixed thereto. Retraction of string 134 transmits a proximal force to eyelet 132 of spring 124, which causes spring 124 to longitudinally expand through lumen 48 of sheath 44. This applies a proximally-directed force to disk 122 that maintains the disk in sealing engagement and substantially conformity with the inner wall of vessel V, and establishes a distally directed restoring spring force according to Hooke's law that would retract spring 124 back to its equilibrium, delivery length absent an external intervening force, e.g., the proximal force applied to string 134.

After spring 124 is expanded a predetermined distance, sheath 44 is proximally retracted to a position just distal to the opening of puncture tract TR, while push rod 138 is held stationary in its current position. Upon removal of sheath 44 from the substantial length of puncture tract TR, expanded spring 124 compressively engages tissue T surrounding the puncture tract. String 134 then is released from push rod 138, e.g., by cutting the string at its proximal end or by pulling the string through and out of eyelet 132 of spring 124, to allow spring 124 to attempt to retract to its equilibrium length within puncture tract TR. During retraction, tissue T, to which spring 124 is compressively engaged, is pinched between adjacent coils of the spring. This engagement of spring 124 with the tissue acts as an external intervening force that prevents the distally directed spring force from retracting spring 124 back to its equilibrium length. Accordingly, spring 124 continues to apply a proximally directed force to disk 122 that sealingly engages and substantially conforms the disk to the inner wall of vessel V to provide hemostasis.

Thereafter, sheath 44 and push rod 138 are removed from the patient. String 134 also may be removed from eyelet 132, or may be taped to the skin of the patient, as shown in FIG. 13D, to ensure that spring 124 does not retract back to its equilibrium length, thereby reducing a risk of disengagement of disk 122 from the inner wall of vessel V. If a portion of string 134 is left within the puncture tract, the string preferably biodegrades over time. Bandage B may be affixed over the puncture tract to prevent contamination of the wound.

As discussed previously, spring 124 may include optional barbs, hooks, roughed surfaces, or sharp edges 142 to enhance engagement with tissue T surrounding puncture tract TR. For example, when sheath 44 is retracted from puncture tract TR and spring 124 compressively engages tissue T surrounding the puncture tract, barbs 142 may penetrate the surrounding tissue. This engagement acts as an external intervening force that prevents the distally directed spring force from retracting spring 124 back to its equilibrium length, thereby maintaining application of a proximally directed force on disk 122 that retains it in sealing engagement with the inner wall of vessel V.

As will be apparent to those of skill in the art, the FIGS. described hereinabove are provided merely for the sake of illustration and may not be drawn to scale. Thus, for example, it is expected that the surface area of tissue T contacted by apparatus of the present invention may be reduced or increased. Furthermore, while preferred illustrative embodiments of the present invention are described hereinabove, it will be evident to one skilled in the art that various changes and modifications may be made to the devices and methods disclosed without departing from the invention. For example, instead of providing a two part occlusion device having a nut and a bolt, the nut and bolt each comprising an expandable disk, a two part rivet occlusion device may be provided, each piece of the two part rivet occlusion device comprising an expandable disk. The two parts of the rivet occlusion device may be connected in a manner similar to standard rivets, per se known. It is intended in the appended claims to cover all such changes and modifications which fall within the true spirit and scope of the invention.

What is claimed is:

1. An apparatus for sealing a subcutaneous puncture site of a vessel wherein the subcutaneous puncture site is accessed through a puncture tract that extends through subcutaneous tissue to the subcutaneous puncture site, the apparatus comprising:

a delivery sheath configured to receive an occlusion element and to deliver the occlusion element through the puncture tract extending through the subcutaneous tissue to the subcutaneous puncture site;

the occlusion element comprised of a first disk comprised of a first membrane made of material that is flexible and fluid impermeable, and a first self-expanding wire frame which supports the first membrane, the first wire frame including a first central point, the first membrane and the first wire frame being foldable into a first configuration wherein the first disk is folded within the delivery sheath to permit introduction of the delivery sheath and the folded first disk through the puncture tract of the tissue to the subcutaneous puncture site, and then through the subcutaneous puncture site into the interior of the vessel, and the first membrane and the first wire frame then expanding toward a second configuration once outside of the delivery sheath and inside the vessel in order to unfold so that the first membrane and the first wire frame will position the first disk against the interior wall of the subcutaneous puncture site to facilitate sealing of the puncture site; and a second disk configured for placement within the puncture tract to securely engage the tissue of the puncture tract, and when secured within the puncture tract the second disk exerting a lateral force on the surrounding tissue of the puncture tract and exerting a longitudinal force on the first disk when it is unfolded in order to urge the first disk against the puncture site to facilitate sealing the puncture site, the second disk comprising a second self-expanding wire frame, the second wire frame including a second central point, the second central point of the second wire frame of the second disk being axially adjustable toward and away from the first wire frame of the first disk prior to, throughout, and after deployment so as to advance together as an integral unit through the puncture tract, the second wire frame being foldable into a first configuration wherein the second disk is folded within the delivery sheath to permit introduction of the delivery sheath, the folded second disk, and the folded first disk being advanced together through the puncture tract of the tissue to the subcutaneous puncture site, and then the first disk being introduced through the subcutaneous puncture site into the interior of the vessel, and the second wire frame of the second disk then being self-expanding toward a second configuration once outside the delivery sheath and inside the puncture tract so that the second wire frame of the second disk will exert a lateral force on the surrounding tissue of the puncture tract while also exerting a longitudinal force against the first disk in order to urge the first disk against the interior wall of the subcutaneous puncture site to facilitate sealing of the puncture site, the first central point of the first wire frame of the first disk and the second central point of the second wire frame of the second disk being separated by a first distance in the first configuration and by a second distance in the second configuration, the first distance being larger than the second distance.

2. The apparatus of claim 1, further comprising an actuator coupled to the second disk, the actuator configured to deploy the first disk.

3. An apparatus for sealing a subcutaneous puncture site of a vessel wherein the subcutaneous puncture site is accessed through a puncture tract that extends through subcutaneous tissue to the subcutaneous puncture site, the apparatus comprising:

a delivery sheath configured to receive an occlusion element and to deliver the occlusion element through the puncture tract extending through the subcutaneous tissue to the subcutaneous puncture site; and the occlusion element comprised of
a first disk comprised of
a first membrane made of material that is flexible and fluid impermeable, and
a first self-expanding wire frame which supports the membrane, the first wire frame including a first central point, the first membrane and the first wire frame being foldable into
a first configuration wherein the first disk is folded within the delivery sheath to permit introduction of the delivery sheath and the folded first disk through the puncture tract of the tissue to the subcutaneous puncture site, and then through the subcutaneous puncture site into the interior of the vessel, and
the first membrane and first wire frame then being self-expanding once outside of the delivery sheath and inside the vessel in order to unfold so that the first membrane and the first wire frame will position the first disk against the interior wall of the subcutaneous puncture site to facilitate sealing of the puncture site; and a second disk for placement within the puncture tract to securely engage the tissue of the puncture tract, and when secured within the puncture tract the second disk exerting a lateral force on the surrounding tissue of the puncture tract and exerting a longitudinal force on the first disk when it is unfolded in order to urge the first disk against the puncture site to facilitate sealing the puncture site, the second disk comprising a second self-expanding wire frame, the second wire frame including a second central point, the second central point of the second wire frame being axially adjustable toward and away from the first wire frame of the first disk prior to, and throughout deployment so as to advance together as an integral unit through the puncture tract and to facilitate repositioning of the device at the subcutaneous puncture site, the second wire frame being foldable into a first configuration wherein the second disk is folded within the delivery sheath to permit introduction of the delivery sheath, the folded second disk, and the folded first disk being advanced together through the puncture tract of the tissue to the subcutaneous puncture site, and then introduction of the first disk through the subcutaneous puncture site into the interior of the vessel, and the second wire frame of the second disk then being self-expanding once outside of the delivery sheath and inside the puncture tract so that the second wire frame of the second disk will exert a lateral force on the surrounding tissue of the puncture tract while also exerting a longitudinal force against the first disk in order to urge the first disk against the interior wall of the subcutaneous puncture site to facilitate sealing of the puncture site the first central point of the first wire frame of the first disk and the second central point of the second wire frame of the second disk being separated by a first distance in the first configuration and by a second distance in a second configuration, the first distance being larger than the second distance.

4. The apparatus of claim 1, wherein the occlusion element is configured to be releasably engaged to the interior vessel surface.

5. The apparatus of claim 1, wherein the wire frame comprises a plurality of separate petals.

6. The apparatus of claim 5, wherein the separate petals each have rounded outer edges.

7. The apparatus of claim 6, wherein each petal is separately formed by one or more wires.

8. The apparatus of claim 7, wherein each petal is joined to the other petals at the central point comprising a joint.

9. The apparatus of claim 1, wherein the first disk is configured to engage tissue.

10. The apparatus of claim 1, wherein the occlusion element comprises barbs, hooks, sharp edges, or roughened surfaces.

11. The apparatus of claim 1, further comprising a coagulant-enhancing agent disposed on the second disk.

12. The apparatus of claim 1, wherein at least a portion of the apparatus comprises a biodegradable material.

13. The apparatus of claim 1, wherein the apparatus is configured to be released from engagement with the interior vessel surface after deployment of the apparatus, thereby permitting the apparatus to be repositioned.

14. The apparatus of claim 3, wherein the occlusion element is configured to be releasably engaged to the interior vessel surface.

15. The apparatus of claim 3, wherein the wire frame comprises a plurality of separate petals.

16. The apparatus of claim 15, wherein the separate petals each have rounded outer edges.

17. The apparatus of claim 16, wherein each of petal is separately formed by one or more wires.

18. The apparatus of claim 17, wherein each petal is joined to the other petals at the central point, the central point comprising a joint.

19. The apparatus of claim 3, wherein the first disk is configured to engage tissue.

20. The apparatus of claim 3, wherein the occlusion element comprises barbs, hooks, sharp edges, or roughened surfaces.

21. The apparatus of claim 3, further comprising a coagulant-enhancing agent disposed on the second disk.

22. The apparatus of claim 3, wherein at least a portion of the apparatus comprises a biodegradable material.

23. The apparatus of claim 3, wherein the apparatus is configured to be released from engagement with the interior vessel surface after deployment of the apparatus, thereby permitting the apparatus to be repositioned.

24. An apparatus for sealing a subcutaneous puncture site of a vessel wherein the subcutaneous puncture site is accessed through a puncture tract that extends through subcutaneous tissue to the subcutaneous puncture site, the apparatus comprising:
- a delivery sheath configured to receive an occlusion element and to deliver the occlusion element through the puncture tract extending through the subcutaneous tissue to the subcutaneous puncture site; and
- the occlusion element comprised of
    - a first disk comprised of
        - a first membrane made of material that is flexible and fluid impermeable, and
        - a first self-expanding wire frame which supports the membrane, the first wire frame including a first central point, the first membrane and the first wire frame being foldable into
            - a first configuration wherein the first disk is folded within the delivery sheath to permit introduction of the delivery sheath and the folded first disk through the puncture tract of the tissue to the subcutaneous puncture site, and then through the subcutaneous puncture site into the interior of the vessel, and
            - the first membrane and first wire frame then being self-expanding once outside of the delivery sheath and inside the vessel in order to unfold so that the first membrane and the first wire frame will position the first disk against the interior wall of the subcutaneous puncture site to facilitate sealing of the puncture site
    - a connecting member; and
    - a second disk for placement within the puncture tract to securely engage the tissue of the puncture tract, and when secured within the puncture tract the second disk exerting a lateral force on the surrounding tissue of the puncture tract and exerting a longitudinal force on the first disk when it is unfolded in order to urge the first disk against the puncture site to facilitate sealing the puncture site, the second disk comprising
        - a second self-expanding wire frame, the second wire frame including a second central point, the second central point of the second wire frame being axially adjustable toward and away from the first wire frame of the first disk by the connecting member prior to, throughout, and after deployment so as to advance together as an integral unit through the puncture tract and to facilitate the separation of the first central point and the second central point from engagement with each other and separation of the occlusion element with the interior vessel surface, thereby permitting the apparatus to be repositioned, the second wire frame being foldable into
            - a first configuration wherein the second disk is folded within the delivery sheath to permit introduction of the delivery sheath, the folded second disk, and the folded first disk being advanced together through the puncture tract of the tissue to the subcutaneous puncture site, and then introduction of the first disk through the subcutaneous puncture site into the interior of the vessel, and
        - the second wire frame of the second disk then being self-expanding once outside of the delivery sheath and inside the puncture tract so that the second wire frame of the second disk will exert a lateral force on the surrounding tissue of the puncture tract while also exerting a longitudinal force against the first disk in order to urge the first disk against the interior wall of the subcutaneous puncture site to facilitate sealing of the puncture site
        - the first central point of the first wire frame of the first disk and the second central point of the second wire frame of the second disk being separated by a first distance in the first configuration where the first disk and second disk are deployed and the first disk engages the inner vessel wall and by a second distance in a second configuration, the first distance being larger than the second distance.

* * * * *